United States Patent
He et al.

(10) Patent No.: US 12,303,515 B2
(45) Date of Patent: May 20, 2025

(54) PIM1 INHIBITORS FOR USE IN TREATMENT OF VIRAL INFECTION AND PHARMACEUTICAL COMPOSITIONS THEREOF

(71) Applicant: City University of Hong Kong, Hong Kong (CN)

(72) Inventors: Ming-Liang He, Hong Kong (CN); Ying Chen, Hong Kong (CN); Fanghang Zhou, Hong Kong (CN); Qianya Wan, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 841 days.

(21) Appl. No.: 17/594,707

(22) PCT Filed: Apr. 30, 2020

(86) PCT No.: PCT/CN2020/088009
§ 371 (c)(1),
(2) Date: Oct. 27, 2021

(87) PCT Pub. No.: WO2020/221334
PCT Pub. Date: Nov. 5, 2020

(65) Prior Publication Data
US 2022/0288087 A1    Sep. 15, 2022

Related U.S. Application Data

(60) Provisional application No. 62/840,819, filed on Apr. 30, 2019.

(51) Int. Cl.
| | | |
|---|---|---|
| *A61K 31/454* | (2006.01) | |
| *A61K 31/5025* | (2006.01) | |
| *A61K 31/551* | (2006.01) | |
| *A61K 31/7088* | (2006.01) | |
| *A61P 31/14* | (2006.01) | |

(52) U.S. Cl.
CPC .......... *A61K 31/551* (2013.01); *A61K 31/454* (2013.01); *A61K 31/5025* (2013.01); *A61K 31/7088* (2013.01); *A61P 31/14* (2018.01)

(58) Field of Classification Search
CPC ................ A61K 31/551; A61K 31/454; A61K 31/7088; A61P 31/14
See application file for complete search history.

(56) References Cited

PUBLICATIONS

About Enterovirus A-71. Non-polio Enterovirus. CDC. p. 1-3. downloaded from https://www.cdc.gov/non-polio-enterovirus/about/about-enterovirus-a-71.html. (Year: 2024).*
Lin et al. Antivirals and vaccines for Enterovirus A71. Journal of Biomedical Science (2019) 26:65, p. 1-10 (Year: 2019).*
Baggen et al. The life cycle of non-polio enteroviruses and how to target it. Nature Reviews, Microbiology. vol. 16:p. 368-381 (Year: 2018).*
Jasamai et al. Current Prevention and Potential Treatment Options for Dengue Infection. J Pharm Pharm Sci (www.cspsCanada.org ) 22, 440-456 (Year: 2019).*
Zakaria et al. Cellular Targets for the Treatment of Flavivirus Infections. Front. Cell. Infect. Microbiol., p. 1-11 (Year: 2018).*
Park et al. Pim Kinase Interacts with Nonstructural 5A Protein and Regulates Hepatitis C Virus Entry. Journal of Virology. vol. 89, No. 19, p. 10073-10086 (Year: 2015).*
Human Rhinovirus 16, VR-283. ATCC Product Sheet. p. 1-5 (Year: 2022).*
Miyakawa et al. PIM kinases facilitate lentiviral evasion from SAMHD1 restriction via Vpx phosphorylation. Nature Communications 10:1844, p. 1-12 (Year: 2019).*
Wichit et al. SAMHD1 Enhances Chikungunya and Zika Virus Replication in Human Skin Fibroblasts. Int. J. Mol. Sci. 2019, 20, 1695, p. 1-18 (Year: 2019).*
Maaike de Vries et al. Inhibition of Pim 1 kinase, new therapeutic approach in virus-induced asthma exacerbations European Respiratory Journal Dec. 2, 2013 vol. 47, ISSN: 1399-3003 pp. 783-791.

* cited by examiner

*Primary Examiner* — Taeyoon Kim
(74) *Attorney, Agent, or Firm* — S&F/WEHRW

(57) ABSTRACT

A Pim-1 proto-oncogene, serine/threonine kinase (PIM1) inhibitor for use in the treatment of a viral infection or use of said PIM1 inhibitor in the preparation of a medicament for said treatment. A method of treating a human afflicted with a viral infection. The method comprises administering, to the human, an effective antiviral amount of a PIM1 inhibitor. A pharmaceutical composition for treating a viral infection comprising a PIM1 inhibitor and a pharmaceutically acceptable excipient.

5 Claims, 9 Drawing Sheets
Specification includes a Sequence Listing.

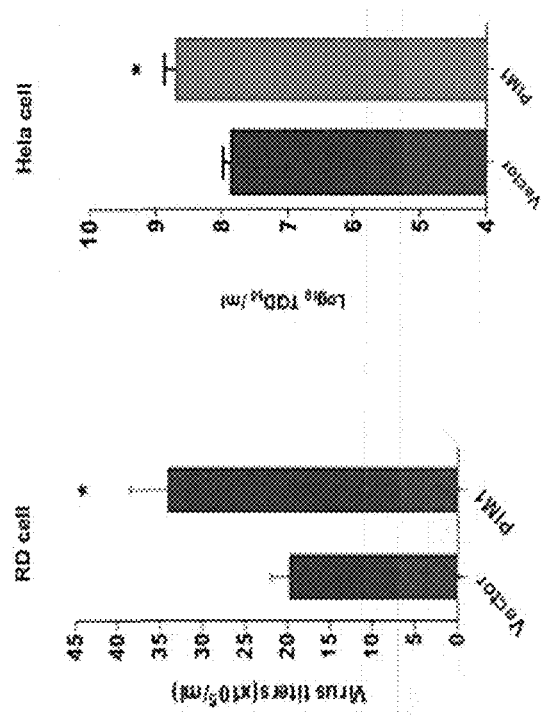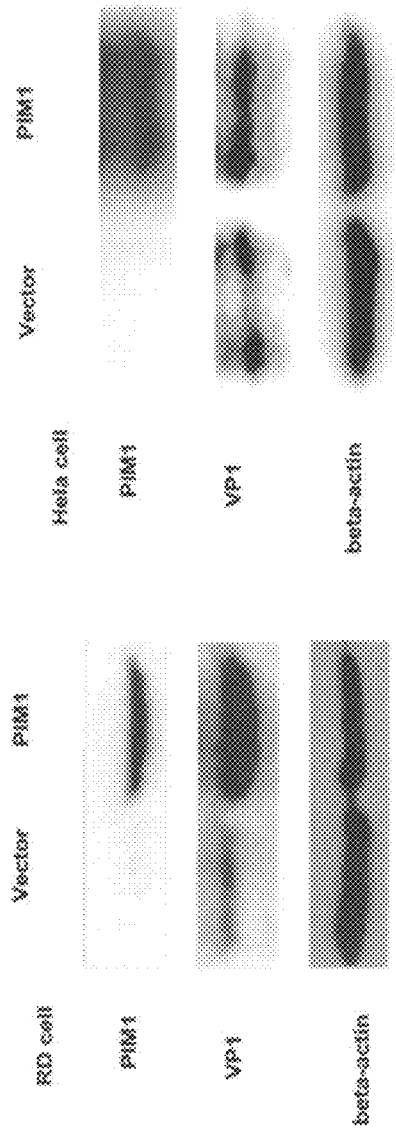
FIG. 3A
FIG. 3B
FIG. 3C
FIG. 3D

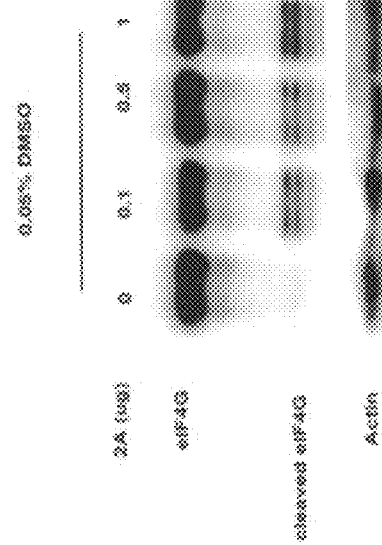
FIG. 6B
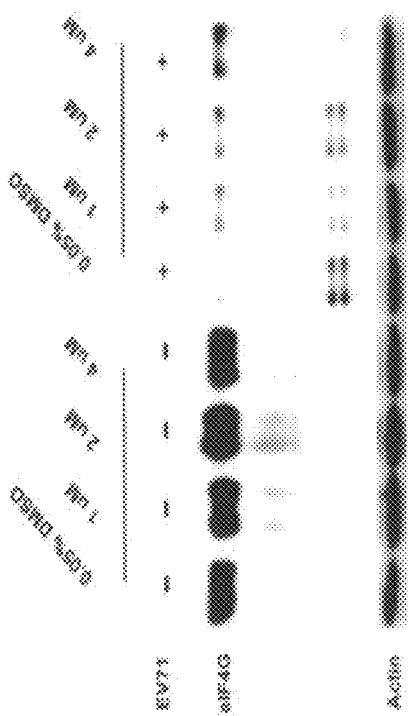
FIG. 6A
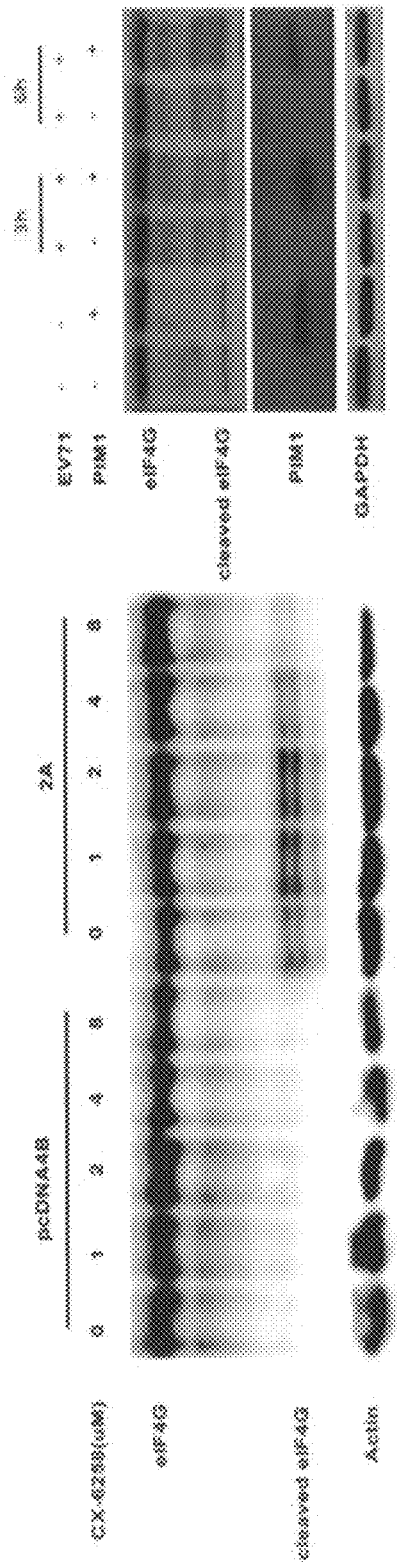
FIG. 6D
FIG. 6C

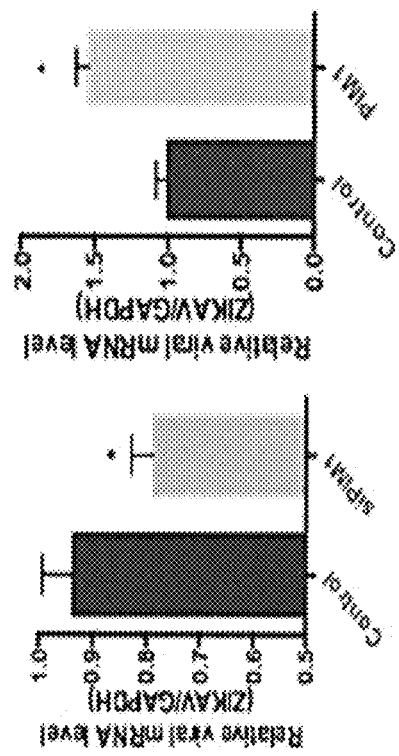
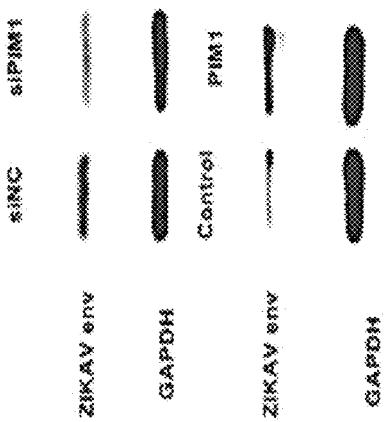
FIG. 8A
FIG. 8B
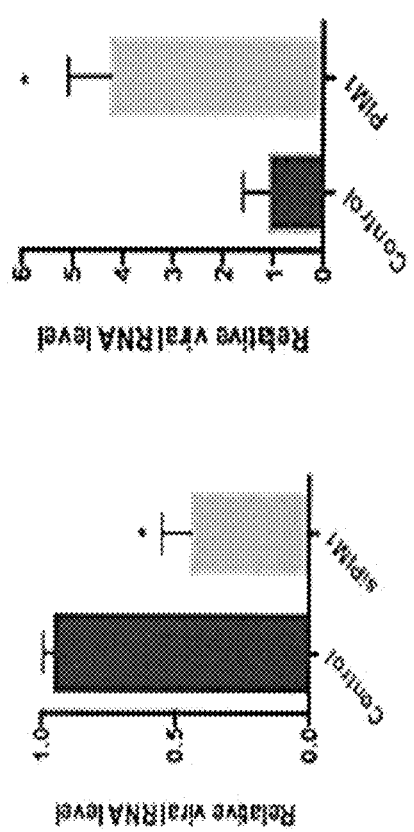
FIG. 8C

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:

```
<223> OTHER INFORMATION: Synthesized

<400> SEQUENCE: 1
aaccuucgaa gaaauccaga accau                                          25

<210> SEQ ID NO 2
<211> LENGTH: 25
<212> TYPE: DNA
<213> ORGANISM: Artificial Sequence
<220> FEATURE:
<223> OTHER INFORMATION: Synthesized

<400> SEQUENCE: 2
augguucugg auuucuucga agguu                                          25

<210> SEQ ID NO 3
<211> LENGTH: 26
<212> TYPE: DNA
<213> ORGANISM: Artificial Sequence
<220> FEATURE:
<223> OTHER INFORMATION: Synthesized

<400> SEQUENCE: 3
guaugauaug guguguggag auauuc                                         26

<210> SEQ ID NO 4
<211> LENGTH: 26
<212> TYPE: DNA
<213> ORGANISM: Artificial Sequence
<220> FEATURE:
<223> OTHER INFORMATION: Synthesized

<400> SEQUENCE: 4
gaauaucucc acacaccaua ucauac                                         26
```

PIM1 INHIBITORS FOR USE IN TREATMENT OF VIRAL INFECTION AND PHARMACEUTICAL COMPOSITIONS THEREOF

CROSS REFERENCE TO RELATED APPLICATIONS

This application is a National Phase entry application of PCT International Application No. PCT/CN2020/088009, filed Apr. 30, 2020, which claims priority to U.S. Provisional Patent Application No. 62/840,819, filed Apr. 30, 2019, the entire disclosures of which are herein expressly incorporated by reference.

TECHNICAL FIELD

The present invention relates to PIM1 inhibitors in treatment of one or more viral infections including, but not limited to, an infection caused by a RNA virus. The present invention also relates to a composition having a PIM1 inhibitor.

BACKGROUND

Viral infections cause a number of severe diseases threatening human health. Millions of death cases reported from different virus infections annually. Enterovirus A11 ("EV-A71 or EVT1") is a human pathogen that causes hand, foot and mouth disease ("HFMD") and fatal neurological diseases without effective treatment. Since 2008, the continuous large epidemics of HFMD caused by EV-A71 and Coxsackievirus A16 ("CVA16") infection became a growing threat to public health in China. In 2012, there are total of ~2,190,000 cases of HFMD were identified, with more than 500 deaths. Clinical observations from HFMD epidemics indicate EV-A71 are the major causative agent for severe and dead cases.

EV-A71 is a typical positive strand RNA virus and belongs to the picomaviridae family. After first identified in 1969 in California, EV-A71 infection and related diseases have been reported world widely. In most common cases, EV-A71 infection causes HFMD which is self-limited and mild disease. However, EV-A71 sometimes could be an etiological agent of neurological diseases such as meningitis, encephalitis, monoplegia, acute flaccid paralysis and even lead to death especially among children under 5 years old.

It is well known that initiation of EV-A71 proteins translation is driven by the internal ribosome entry site ("IRES") in the 5-UTR in a cap-independent mariner. Also, EV-A71 contains a type I IRES with five stern-loops (domain II-VI) which functions when eukaryotic initiation factors eIF4G is cleaved. The viral translation process is highly promoted by viral protein 2A proteinase ($2A^{pro}$). Previously, 2A showed a function to cleave eIF4G and then enhanced viral IRES activity. Further, the factors regulated IRES activity were named as IRES trans-acting factors ("ITAFs"), such as upstream element binding protein (FBP) 1-3, hnRNP K and hnRNP A.

To date, no effective treatment could be applied to EV-A71 infection and the knowledge on EV-A71 infection mechanism is very limited. Microarray assay is one of powerful ways to study the transcriptional responses of cells subjected to a variety of environmental stimuli, including viral infection. By using the high-density cDNA microarray, it is possible to characterize the entire transcriptomic profile of the cell response to viral pathogenesis and provide an insight into the genes involved in host cell antiviral responses, genes that are essential for the EV-A71 replication cycle and genes that contribute to EV-A71-associated pathology. Microarray expression profiling was used to identify host genes regulated EV-A71 infection in several studies. However, due to the limits of technology only subsets of the human transcriptosome were typically detected, and some important genes relate to EV-A71 infection may be neglected. Moreover, the biological significance of cellular gene expression patterns was still less known, due to the role of host genes in virus replication cycle including the processes of viral entry, assembly, and exit was still uncovered.

Zika virus ("ZIKV") is an RNA virus and belongs to flavivirus firstly isolated in 1947 in Uganda. After that, there are several Zika virus infection outbreaks worldwide, such as Yap island, Easter Island, New Caledonia and America. The virus has gotten global attention due to the virus caused public health problems. Previously documents reported ZIKV could through sexual and vertical transmission and cause several clinical diseases. People also found that ZIKV could induce Guillain-Barré syndrome ("GBS") in adults and severe clinical symptoms in fetuses and infants such as, microcephaly and congenital malformations. However, there is still a lack of efficient approaches to control ZIKV infection and protective vaccine or therapeutic ways.

There are several ways to address different viral infections. Specific pharmaceutical chemicals are one of the effective approaches for treating viral infections. However, only limited chemical drugs are designed for treating viral infection due to a number of difficulties. Accordingly, there remains a need for compounds and methods for treating one or more viral infections.

SUMMARY OF THE INVENTION

The following presents a summary to provide a basic understanding of one or more embodiments of the invention. This summary is not intended to identify key or critical elements, or delineate any scope of the particular embodiments or any scope of the claims. Its sole purpose is to present concepts in a simplified fortn as a prelude to the more detailed description that is presented later. In one or more embodiments described herein, systems, computer-implemented methods, apparatuses and/or computer program products that can treat, viral infections are described.

According to an aspect of the present invention, there is provided a method of treating a human with a viral infection. The method can comprise administering, to the human, an effective antiviral amount of Pim-1 proto-oncogene, serine/threonine kinase (PIM1) inhibitor.

According to another aspect of the present invention, it relates to a method of inhibiting replication of a viral infection. The method can comprise administering, to a biological cell afflicted with the viral infection, an antiviral amount of a PIM1 inhibitor.

According to a further aspect, the present invention pertains to a method of modulating an internal ribosome entry site activity of a viral infection afflicting a biological cell is provided. The method can comprise controlling a level of a PIM1 within the biological cell.

In another aspect, the present invention relates to a PIM1 inhibitor for use in the treatment of a viral infection.

In a further aspect, the present invention pertains to use of a PMI1 inhibitor in the preparation of a medicament for treating a viral infection.

In a still further aspect, the present invention pertains to a pharmaceutical composition for treating a viral infection comprising a PIM1 inhibitor and a pharmaceutically acceptable excipient.

BRIEF DESCRIPTION OF THE DRAWINGS

FIG. 3A is a plot showing the virus titers of RD cells transfected with a PIM1 expressing plasmid and it demonstrates that ectopic-expression of PIM1 promotes viral replication.

FIG. 3B is a plot showing the virus titers of HeLa cells transfected with a PIM1 expressing plasmid and it demonstrates that ectopic-expression of PIM1 promotes viral replication.

FIG. 3C shows the expression of PIM1 and VP1 in RD cells transfected with a PIM1 expressing plasmid as compared to a control group.

FIG. 3D shows the expression of PIM1 and VP1 in HeLa cells transfected with a PIM1 expressing plasmid as compared to a control group.

FIG. 6A shows the relative expression of eIF4G and cleaved eIF4G in RD cells treated with CK-6258 at different concentrations followed by infection with or without EV-A71 at MOI 10.

FIG. 6B shows the relative expression of eIF4G and cleaved eIF4G in RD cells activated by viral protein 2A at different concentrations.

FIG. 6C shows the relative expression of eIFAG and cleaved eIFAG in HEK 293T cells treated with CX-6258 and with or without co-transfection of viral protein 2A expressing plasmid. The results show that the PIM1 inhibitor CX-6258 inhibits the cleavage of eIF4G cleaved by viral 2A proteinase in accordance with an embodiments herein.

FIG. 6D shows the relative expression of eIFAG, cleaved eIFAG and PIM1 in EV71 infected HEK 293T cells or non-infected cells with or without PIM1 expression plasmid transfection.

FIG. 8A shows the relative expression of ZIKA viral envelop protein (denoted as ZIKAV env) in a siNC group, a siPIM1 group (transfected with siPMI1), a control group (non-treatment group) and a PIM1 group (transfected with PIM1 expressing plasmid).

FIG. 8B is a plot showing the relative viral mRNA level in the groups mentioned in FIG. 8A.

FIG. 8C shows two plots illustrating the relative viral mRNA level when PIM1 was knockdowned by transfection with siPIM1 and when PIM1 was overexpressed. The results demonstrate that silence of PIM1 expression blocks Zika infection and over expression of PIM1 promotes Zika viral replication.

DETAILED DESCRIPTION OF THE INVENTION

Figure 1C:
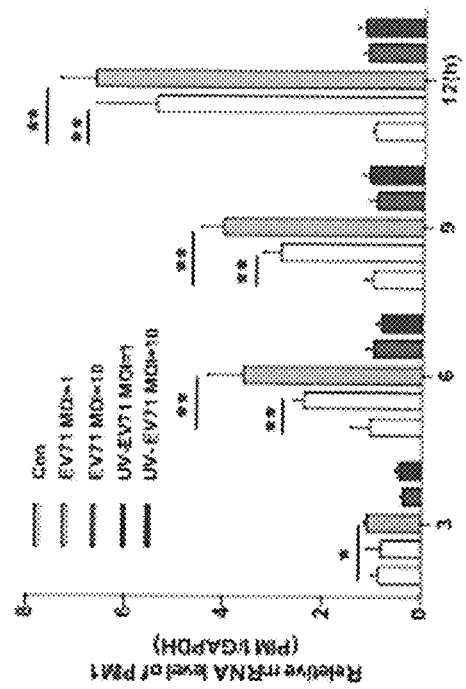
FIG. 1C is a plot showing the relative mRNA level of PIM1 in RD cells infected with EV-A71 or inactive EV-A71 respectively at MOI=1 or MOI=10, as compared to a control group. The results demonstrate that EV-A71 infections promote PIM1 mRNA expression level.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

According to the present invention, there is provided a PIM1 inhibitor for use in the treatment of a viral infection. The viral infection is preferably a RNA viral infection, i.e. an infection caused by a RNA virus. The RNA viral infection may be characterized by an internal ribosome entry site (IRES) activity that is enhanced via cleavage of eukaryotic initiation factor 4 G (eIF4G) by viral protein 2A proteinase. In one or more embodiments herein, the RNA viral infection may be caused by a flavivirus, an enterovirus, or a hepatitis virus.

In an embodiment, the viral infection is selected from a group consisting of a Zika virus infection, a hepatitis virus infection, a West Nile virus infection, a Dengue virus infection, a Tick-borne Encephalitis virus infection, a yellow fever virus infection, and an enterovirus A71 infection. In a particular embodiment, the viral infection is caused by an enterovirus A71 or a Zika virus.

It would be appreciated that the PIM1 inhibitor as discussed herein would be useful to inhibit the development, and delay pathological progress of the illness or disorder caused by a viral infection. In particular, the PIM1 inhibitor of the present invention can diminish the replication of a virus within an individual, and thus prevent or delay the virus invasion.

The PIM1 inhibitor of the present invention refers to a substance which may be a nucleic acid, a homologue or a fragment thereof, or a compound including a complex, capable of inhibiting the expression of PIM1 in the target tissue or cell. It is found that cells infected by a virus particularly EV-A71 have an increased mRNA expression of PIM1 and that the increased level of PIM1 enhances viral activity. The inventors conducted some tests to determine the role of PIM1 in viral activity.

GENECHIP® Human Gene 1.0 ST Array which covering 28,869 genes were employed to analyze the molecular changes after EV-A71 infection. According to microarray analysis, 173 genes changed by at least 1.5 fold, and most of these host genes were up-regulated following virus infection. PIM1 gene which was up- regulated in response to EV-A71 infection was selected for further functional investigation. As described herein, PIM1 plays critical role in EV71 infection through enhancing internal ribosome entry site (IRES) activity by assisting viral protein 2A cleave eIF4G function, and the inventors also found that PIM1 inhibitors efficiently inhibited viral replication. Further, PIM1 inhibitors can significantly inhibit viral infection replication (e.g., ZIKAV replication). In one or more embodiments, PIM1 kinase can be an antiviral target in host cells, with remarkable virus replication inhibition effects in clinical usage.

In one or more embodiments herein, the PIM1 inhibitor may be a RNA such as, but not limited to, an interfering ribonucleic acid (interfering RNA) particularly a small interfering ribonucleic acid (siRNA), a short hairpin RNA, a microRNA, or a fragment thereof. In an embodiment, the PIM1 inhibitor may include an interfering RNA sequence in particular a siRNA having a nucleic acid sequence selected from SEQ ID NO: 1 to SEQ ID NO: 4, or a combination thereof. The sequences are as shown below and listed in the sequence listing.

```
SEQ ID NO: 1:
AACCUUCGAAGAAAUCCAGAACCAU;

SEQ ID NO: 2:
AUGGUUCUGGAUUUCUUCGAAGGUU;

SEQ ID NO: 3:
GUAUGAUAUGGUGUGUGGAGAUAUUC;
and

SEQ ID NO: 4:
GAAUAUCUCCACACACCAUAUCAUAC.
```

The PIM1 inhibitor may include one or two or more sequences as discussed above. For example, the PIM1 inhibitor may consist of one sequence selected from SEQ ID NO: 1 to SEQ ID NO: 4, or a homologue or a functional variant thereof. In another example, the PIM1 inhibitor may consist of any two sequences selected from SEQ ID NO: 1 to SEQ ID NO: 4, or homologues or functional variants thereof, thereby forming a siRNA duplex for inhibition. In a particular embodiment, the PIM1 inhibitor is a siRNA formed by SEQ ID NO: 1 and SEQ ID NO: 2 or formed by SEQ ID NO: 3 and SEQ ID NO: 4. It would be appreciated that the scope of the invention herein also encompasses homologues as well as functional variants of the above sequences.

In one or more embodiments herein, the PIM1 inhibitor may be a compound, e.g. a chemical inhibitor. The compound may have a structure of Formula (I), Formula (II), Formula (III) or a salt or solvate thereof:

Formula (I)

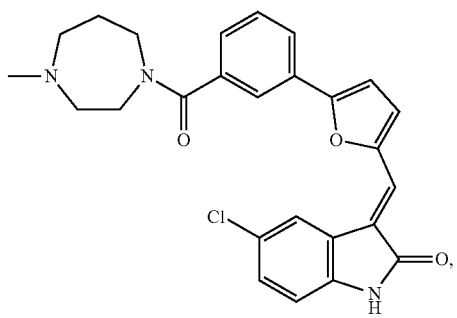

Formula (II)

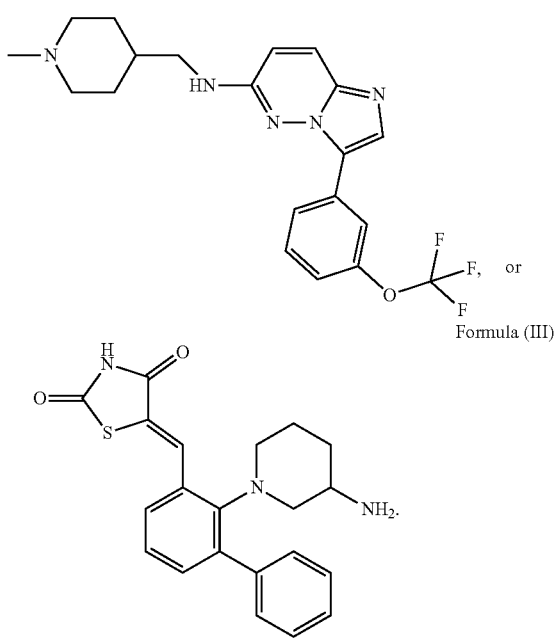

Formula (III)

In particular, a compound having the structure of Formula (I) is CX-6258, a compound having a structure of Formula (II) is SGI-1776, and a compound having a structure of Formula (III) is AZD-1208. Compounds CX-6258, SGI-1776 and AID-1208 were also used in proving the inhibitory effect of a PIM1 inhibitor in viral infection. Accordingly, these compounds are suitable PIM1 inhibitors against viral infections such as against EV-A71 infection. Without intention to be limited by theory, it is found that the PIM1 inhibitors are able to induce ARE/poly(U)-binding/degradation factor 1 (AUF1) accumulation, thereby suppressing IRES activity and subsequently decreasing the reproduction of the virus.

Accordingly, the PIM1 inhibitors are useful in combating viral invasion and can be formulated in a composition for treating a viral infection or alleviating discomfort or illness caused by the rapid growth or replication of the virus in an individual.

The present invention also pertains to use of the PIM1 inhibitor in the preparation of a medicament for treating a viral infection. The inhibitor and the viral infection are as described above.

Moreover, the present invention also pertains to a pharmaceutical composition comprising said PIM1 inhibitor and a pharmaceutically acceptable excipient for administration to a subject in need thereof. The pharmaceutical composition can be provided in solid, semisolid or liquid form, preferably in a liquid form. The pharmaceutical composition can be applied via injection to the subject or particularly to the tissue or cell of concern.

In an embodiment where the PIM1 inhibitor is a nucleic acid comprising one or more sequences selected from SEQ ID NO. 1 to SEQ ID NO. 4, or a homologue or functional variant thereof, the PIM1 inhibitor may be present in a vector such as a recombinant plasmid. The PIM1 inhibitor may also be formulated in a carrier to facilitate suitable administration.

In an embodiment where the PIM1 inhibitor is a compound, e.g. a compound having a structure of Formula (I), Formula (II), Formula (III) or a salt or solvate thereof:

Formula (I)

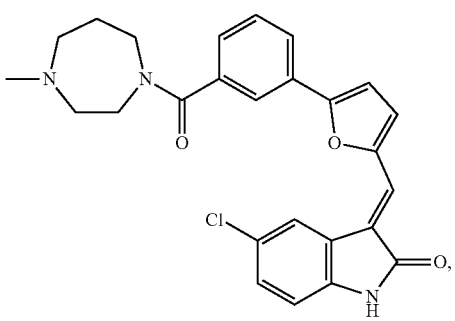

Formula (II)

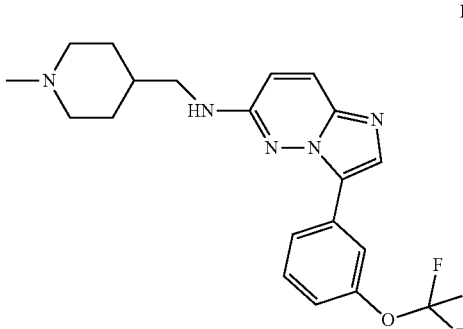

Formula (III)

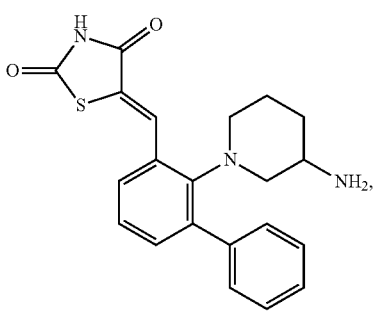

the pharmaceutical composition may include any suitable pharmaceutically acceptable excipient such as, but not limited to, a diluent, a filler, a dye, a lubricant, a preservative, and the like, depending on the route of administration.

The present invention also pertains to a method of treating a subject such as a human suffering from or afflicted with a viral infection. The method includes a step of administering an effective amount particularly an effective antiviral amount of a PIM1 inhibitor as described above to the subject.

The subject may be a mammal and in particular a human. The expressions "effective amount" and "effective antiviral amount" denote an amount sufficient to have a beneficial effect against a viral infection, wherein the exact nature of the result may vary depending on the specific subject. The effective amount of the PIM1 inhibitor of the present invention may depend on the species, weight and gender of the subject, and can be determined by standard procedures. Preferably, the effective amount of a PIM1 inhibitor is able to inhibit the replication or a virus or delay the pathological progress caused by a virus invasion. It would be appreciated that the use of the PIM1 inhibitor may be able to alleviate symptoms associated with a viral infection because it buys time for the immune system of the subject to react against the viral invasion.

Accordingly, there is also provided a method of inhibiting replication of a viral infection as described above. The method comprises administering, to a biological cell afflicted with the viral infection, an antiviral amount of a PIM1 inhibitor as described above. There is further provided a method of modulating an internal ribosome entry site activity of a viral infection as descried above afflicting a biological cell, the method comprising: controlling a level of PIM1 within the biological cell. These methods utilize the PIM1 inhibitor of the present invention as discussed above to combat one or more viral infections.

The following examples and discussion in relation to the experimental results further illustrate the present invention, particularly the use of PIM1 inhibitor in inhibiting viral infection particularly suppressing viral replication. A skilled person will understand that the above embodiment or the discussion below is not intended to be limiting.

Materials and Methods

Virus and cells: RD cells (ATCC number CCL-136) and 293T cells were maintained in Dulbecco's modified Eagle's medium ("DMEM") containing 10% fetal bovine serum ("FBS") with 100 U/ml penicillin and 100 ng/ml streptomycin. EV-A71 (SHZH98 strain, GenBank accession number AF302996) was obtained from Shenzhen Center for Disease Control and Prevention, Shenzhen, China. Virus was propagated as previously described.

Microarray Analysis: For microarray, RD cells were infected with EV-A71 at MOI of 10 and collected 6 h after inoculation. Normal cells without viral inoculation were set as the control. The experiment was repeated three times independently. Cellular RNA from 6 samples was extracted by using the Qiagen RNeasy Mini Kit according to the manufacturer protocol. Following the quality control, RNA were prepared for microarray analysis by using the Affymetrix GeneChip Human Gene 1.0 ST Array, which interrogates 28,869 genes across 764,885 distinct probes and contains greater than 99% of sequences present in the RefSeq database. Two-way analysis of variance (ANOVA) of the genes was performed with a P-value cut-off of less than 0.05 to determine significantly up- and down-regulated genes during EV-A71 infection. Genes with fold change >1.5 or <−1.5 between EV-A71- and mock-infected samples were selected.

Quantitative Reverse transcription Polymerase Chain Reaction ("RT-qPCR"): To validate the microarray results, 12 representative genes were selected for further evaluation by real-time quantitative RT-qPCR. 1 jug of total RNA from samples used in the microarray experiments was subjected to reverse transcription using ImProm-II™ Reverse Transcription System. RT-q PCR was carried out in the ABI 7500 Real-Time PCR system with Power SYBR Green Master Mix (Applied Biosystems, USA), using the following program: 50° C. for 2 min, 95° C. for 10 min followed by 45 cycles of 95° C. for 15 s and 60° C. for 1 min.

Sets of primers for these 12 genes are available upon request. All samples were run in triplicate and the experiment was repeated three times. The messenger RNA (mRNA) level of each target gene was normalized to the mRNA copies of GAPDH in the same sample and results were expressed as a percentage of the negative control (set as 1).

RNA interference: RNA interference was carried out using siRNA purchased from Genepharma (ShangHai, China). Two separate siRNA corresponding to the PIM1 mRNA was used to inhibit endogenous PIM1 expression:

```
si-PIM1-1-Sense (SEQ ID NO: 1):
AACCUUCGAAGAAAUCCAGAACCAU, si-PIM1-1-Antisense (SEQ ID NO: 2):
GGUUCUGGAUUUCUUCGAAGGUU;

si-PIM1-2-Sense (SEQ ID NO: 3):
GUAUGAUAUGGUGUGUGGAGAUAUUC, si-PIM1-2-Antisense (SEQ ID NO: 4):
GAAUAUCUCCACACACCAUAUCAUAC.
```

Scramble siRNA was used as the control. Transfection of siRNA was performed according to the manufacturer's instructions. In brief, cells at 50% confluence were transfected with 40 nM siRNA using the Lipofectamine 2000.

Figure 4C:
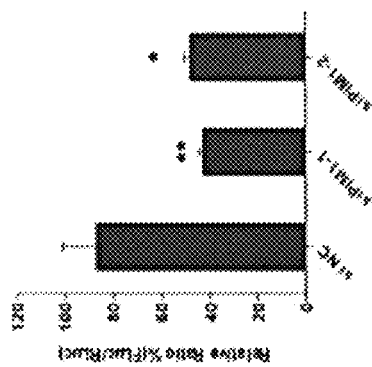
FIG. 4C is a plot showing the relative ratio of FLuc expression to RLuc expression in cells transfected with siPIM1-1 or siPIM1-2 as compared to a control group.
Figure 4B:
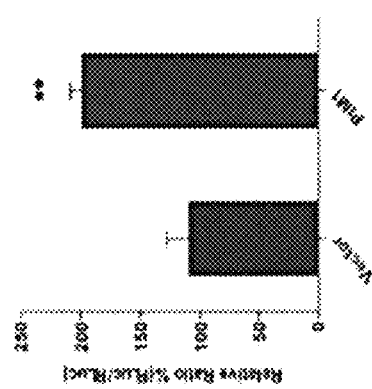
FIG. 4B is a plot showing the relative ratio of Fluc expression to RLuc expression in cells transfected with a PIM1 expressing plasmid as compared to a control group.
Figure 4A:
FIG. 4A is a schematic diagram showing the arrangement of a dicistronic reporter plasmid used in evaluating EV-A71 IRES activity when PIM1 is modulated.

Plasmids construction: Human PIM1 (Accession NM_001243186) was amplified using Platinums Taq DNA Polymerase high fidelity (Invitrogen, USA). The PGR product was cloned into pcDNA4/HisMax B (Invitrogen, USA) vector between BamHI and Xbarl sites. The EV-A71 report plasmid pRIRESF was constructed as follows: Renilla Luciferase gene ("RLuc") was inserted into pcDNA4/HisMax B between BamHI and EcoRV sites; EV-A71 IRES was amplified from EV-A71 virus strain (SHZH98). Also, Firefly Luciferase gene ("FLuc") was amplified by using primer which has overlap sequence with the C-terminal of EV-A71 IRES. Finally, the construct IRES-FLuc were then amplified by using overlap PGR, and inserted into the downstream of the Renilla Luciferase gene by using EcoR V and Xba I. The control plasmid pRF was constructed in similar way except containing EV-A71 IRES in the upstream of FLuc gene (FIG. 4A). The Fluc gene was amplified and then inserted into the downstream of the Renilla Luciferase gene by using EcoR V and Xba I. All primers used in plasmids construction are available upon request.

Western blotting: Cells were lysed Nonidet-P40 (NP-40) buffer (150 mM sodium chloride, 1.0% NP-40, 50 mM Tris, pH 8.0, IxRoche protease inhibitor cocktail) with occasional vortex. The cell lysates were then eentriffiged to remove debris at 14,000 rpm for 20 min at 4° C. The concentration of proteins in the lysates was determined by Bradford assay (Bio-Rad). Equal amounts of total protein for each sample was loaded and separated by 8%-12% SDS-PAGE and then transferred onto polyvinylidene difluoride (PVDF) membranes (Amersham Biosciences). Membranes were blocked with 5% Bull Serum Albumin (BSA) in TBST (20 mM Tris-HCl, pH 7.4, 150 mM NaCl, 0.1% Tween 20) for 1 h and incubated with specific antibodies. Beta-actin was served as the loading control. Target proteins were detected with corresponding secondary antibodies (Santa Cruz Biotechnology, USA), visualized with a C600 western blot imaging system from Azure Biosystems. Each immunoblot assay was carried out at least three times.

Viral RNA quantification: Entry, replication, package and release of virus were analyzed by calculating different form of EV-A71 viral RNA as previously described. Briefly, the total cellular RNA was isolated for intracellular viral RNA quantification. To calculate the extracellular virions, the culture media of infected cells was firstly harvested and briefly centrifuged to remove cell debris. Viral core particles were then precipitated with 10% polyethylene glycol 8000 containing 0.5 M NaCl at 4° C. overnight. After centrifuging for 30 min at 16,000 g, viral particles were pelleted and treated with 100 μg/ml of RNase A (Sigma, USA). To isolate the intracellular virions, EV-A71 infected cells were lysed with lysis buffer (1% Triton 100 and 1× Roche protease inhibitor cocktail in PBS). Then the cell lysates were used to isolated viral particles as described above. To set up the standard curve of infectious viruses, the viral titers were first determined by CPE assay. Then the viral RNA was extracted from those infectious EV-A71 viruses. RNA was diluted at tenfold serial and used to reflect the calculated PEU from 10 to $1\times10^7$ live virions.

Virus titration: RD cells were seeded into 96-well plates for 24 h before infection, then cells were infected by 100 μl per well of serial 10-fold diluted supernatant in quintuplicate. The 50% tissue culture-infected dose (TCID50) was calculated by the Reed-Muench method after 96 h of infection.

Luciferase assays: 293T cells were plated in 24-well one day before transfection. PIM1 over expression plasmid or corresponding siRNA were transfected. 24 hours later, cells were next transfected with PRIE or PRE reporter plasmids. Two days after first-round transfection, cell extracts were prepared in passive buffer (Promega, USA) and assayed for Renilla luciferase ("RLuc") and Firefly luciferase ("ELuc") activity in a Lumat LB9507 bioluminometer using a dual-luciferase reporter assay (Promega) according to the manufacturer's instructions.

3-(4,5-dimethylthiazol-2-yl)-2,5-diphenyl tetrazolium bromide (MTT) assay: Cell viability was assessed by 3-(4,5-dimethylthiazol-2-yl)-2,5-diphenyl tetrazolium bromide (MTT) assay. After RD cells were grown in 96-well plates and treated with PIM1 inhibitors, 20 μl of MTT (5 mg/ml) was added to each well, and cells were further incubated for an additional 4 h at 37° C. Next, the medium was carefully removed and subsequently 100 μl of Dimethyl Sulfoxide were added. The optical density was measured at a wavelength of 570 am.

Isolation of nuclear and cytoplasmic protein: Briefly, Cells (5 to $10\times10^6$ cells) were collected, and washed by PBS three times. And then extract the cytoplasm proteins by cytoplasmic extract (CE) buffer (HEPES [10 mM] pH 7.9, KCl [10 mM], EDTA [0.1 mM], NP-40 0.3% (add just before use), protease inhibitors Ix (add just before use)). After that, using nuclear extract (NE) buffer (HEPES [20 mM] pH 7.9, NaCl [0.4 M], EDTA [1 mM], Glycerol 25%, Protease Inhibitors 1x (add just before use)) to extract nuclear proteins.

Fluorescence microscopy: Fluorescence microscopy were performed as described. RD cells grown on glass cover slips were pretreated with PIM1 inhibitor CX-6258, the culture media were removed, and the cells washed three times with PBS. The cells on the coverslip were fixed with 3.7% (wt/vol) formaldehyde at room temperature for 20 min. After being washed three times with PBS, cells on the coverslip were pemieabilized with 0.5% Triton X-100 at room temperature for 5 min and washed again three times with PBS. For AUF1 immunostaining, the samples were blocked in solution (PBS, containing 5% bovine serum albumin [BSA]) for 60 min at room temperature and then incubated with anti-AUF1 (ab50692, San Francisco) for 1.5 h at room temperature and washed three times with PBS. The samples were then reacted with rhodamine (tetramethyl rhodamine isothiocyanate [TRITC])-conjugated goat anti-rat IgG (Jackson ImmunoResearch Laboratories, Inc.) for 1 h at room temperature.

After being washed with PBS, the samples were treated with DAPI for 5 min at room temperature and washed again with PBS three times. Finally, coverslips with adhered cells were placed on a glass slide and sealed with transparent nail polish. Images were captured by confocal laser scanning microscopy (ZEISS LSM 880 Confocal Microscope).

Statistical analysis: Results were expressed as mean standard deviation (SD). All statistical analyses were carried out with SPSS, version 16.0 software (SPSS Inc.). Two-tailed Student's t test was applied for two group comparisons. A p value <0.05 was considered statistically significant.

Results

Figure 1B:
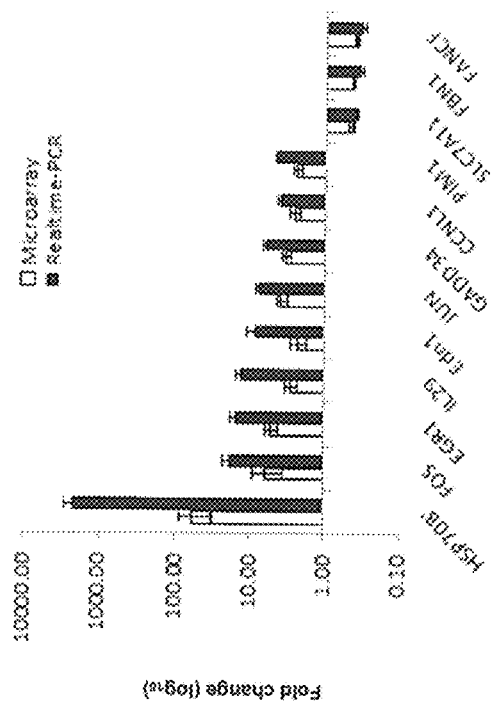
FIG. 1B is a plot showing the fold change of expression of different selected genes including HSP70B', FOS, EGFR1, IL29, Edn1, JUN, GADD 34, CCNL1, PIM1, SLC7A11, FBN1 and FANCF genes, obtained via real-time PCR and microarrays.
Figure 1A:
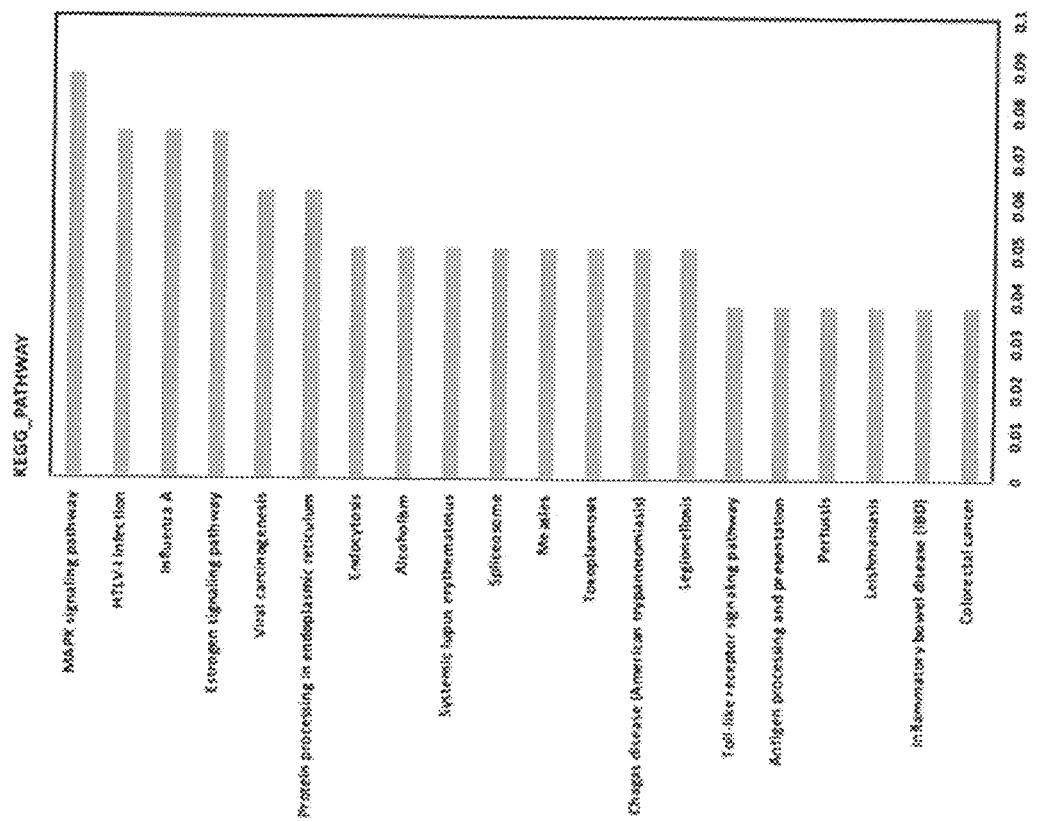
FIG. 1A is a plot showing the percentage of genes involved in KEGG pathway.

Transcriptomic assays upon EV-A71 replication: In various embodiments, RD cells were infected at a high multiplicity of infection (MOI, 10) and total RNA was isolated at 6 hours post infection (p.i.) when virus was undergoing fast replication. The total RNA was used for microarray analysis. Fold changes of gene expression profiles were calculated as described in Materials and Methods. Of these, 267 transcripts were up-regulated while 158 transcripts demonstrated a decrease in expression level greater than 1.5-fold. 79 representative transcripts which were significantly altered were listed and grouped according to their known functions (Table 1). Genes with altered transcriptional patterns belonged to a wide range of functional classes (KEGG pathway). For instance, those involved in cell cycle and immune response were also significantly enriched among genes showing differential expression during EV-A71 infection (e.g., as depicted in FIG. 1A).

Validation of selected gene expression changes during EV-A71 infection: To validate the microarray results, quantitative RT-PCR (RT-qPCR) was performed for 12 genes, which represented transcripts of the various functional clusters. The results from RT-qPCR showed a good correlation with the gene expression data from the microarrays (e.g., as shown in FIG. 1B). To reveal the regulation pattern of PIM1 in EV-A71 infection, the mRNA level of PIM1 was analyzed during the process of viral infection. RD cells were infected with EV-A71 or inactive EV-A71 (UV light inactive virus, negative control) at MOI of 10, and the cellular mRNA was extracted at different time points p.i. Results showed that the nRNA level of PIM1 increased as early as 3 hours p.i., and significantly up-regulation was observed at 6 and 9 hours p.i. as compared with the control group (e.g., as shown in FIG. 1C).

Figure 2A:
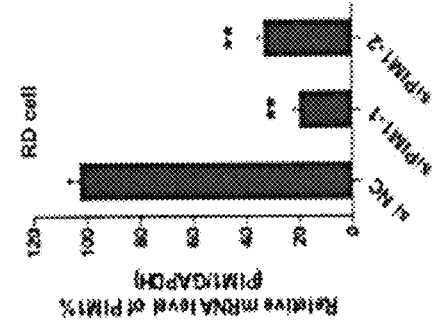
FIG. 2A is a plot showing the relative mRNA level of PIM1 in RD cells transfected with siPIM1-1 and siPIM1-2 specific siRNAs as compared to a control group, (denoted as si NC).
Figure 2B:
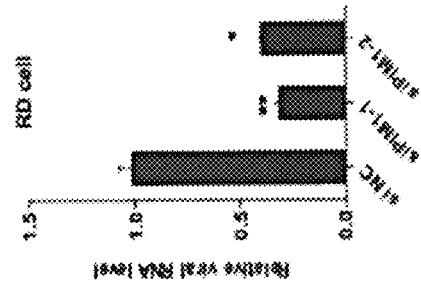
FIG. 2B is a plot showing the relative viral RNA level in RD cells transfected with siPIM1-1 and siPIM1-2 specific siRNAs as compared to a control group, (denoted as si NC).
Figure 2C:
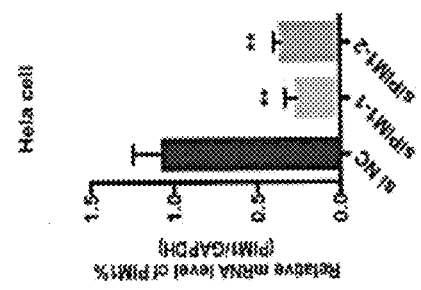
FIG. 2C is a plot showing the relative mRNA level of PIM1 in HeLa cells transfected with siPIM1-1 and siPIM1-2 specific siRNAs as compared to a control group, (denoted as si NC).

Inhibition of EV-A71 replication by knockdown of PIM1: To determine whether PIM1 was required during EV-A71 infection, RNAi approach was employed to knockdown the level of PIM1. 48 hours after siRNA transfection. PIM1 mRNA level was reduced in RD and HeLa cells by 20% and 30% by siPIM1-1 and siPIM1-2 specific siRNAs respectively in comparison with non-targeting sequences, as quantified by RT-qPCR (p<0.01) (FIGS. 2A & 2C). MTT (3-(4,5-dimethylthiazol-2-yl)-2,5-diphenylietrazoliurn bromide) assays were performed to determine the cell viability upon PIM1 silencing. There was no difference on cells number between siPIM1 transfected cells and non-target RNA transfected cells at 24 hours and 48 hours post transfection (data not shown).

Figure 2D:
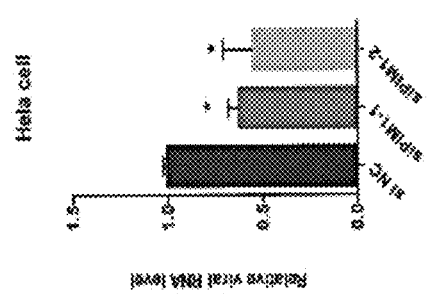
FIG. 2D is a plot showing the relative viral RNA level in HeLa cells transfected with siPIM1-1 and siPIM1-2 specific siRNAs as compared to a control group, (denoted as si NC).
Figure 2E:
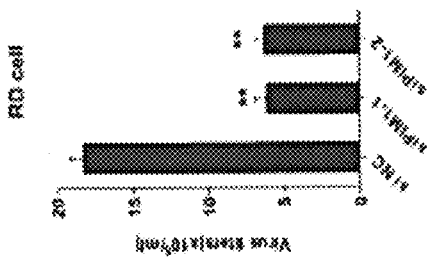
FIG. 2E is a plot showing the viral titre of RD cells transfected with siPIM1-1 and siPIM1-2 specific siRNAs as compared to a control group, (denoted as si NC).
Figure 2H:
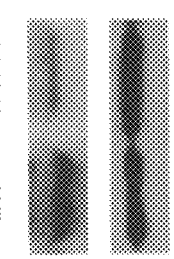
FIG. 2H shows the expression of viral protein VP1 in RD cells infected by EV71, with or without siPIM1-1 transfection.
Figure 2I:
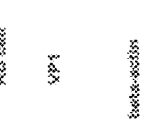
FIG. 2I shows the expression of viral protein VP1 in RD cells infected by EV71, with or without siPIM1-1 transfection.
Figure 2G:
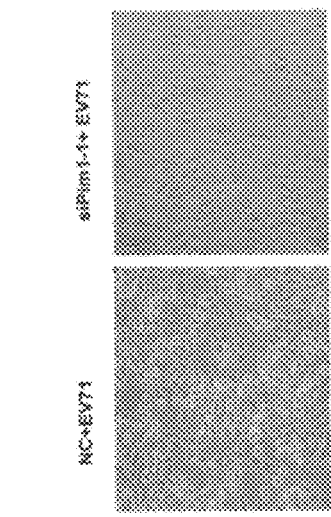
FIG. 2G shows the cytopathic effect of RD cells infected by EV71, with or without siPIM1-1 transfection.
Figure 2F:
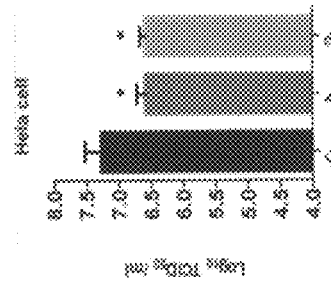
FIG. 2F is a plot showing the 50% tissue culture-infected dose (TCID50) calculated by by the Reed-Muench method after 96 h of infection of HeLa cells.

RD or HeLa cells were transfected with siPIM1-1 or siPIM1-2 specific siRNA or non-target siRNA as a control. After 24 h transfection, cells were then infected with EV-A71 at MOI of 0.01. As shown in FIGS. 2B and 2D, extracellular viral RNA levels were strongly decreased in PIM1-specific siRNA treated cells in comparison with cells treated with non-targeting sequences (p<0.01). The viral titre was also determined after silencing PIM1. The results showed that the viral titer was significantly decreased in both RD and HeLa cells after knockdown of PIM1 (e.g., as shown in FIGS. 2E and 2F). The cytopathic effects were taken in RD cells (e.g., as shown in FIG. 2G). The viral protein VP1 level was shown in FIGS. 2H and 2I after knockdown of PIM1.

Based on the results, it is demonstrated that silencing PIM1 expression can block EV-A71 infection in accordance with one or more embodiments described herein.

Promoting EV-A71 replication by ectopic expression of PIM1: To further validate the function of PIM1 on virus replication, the inventors conducted gain of function studies by ectopic expression of PIM1 by transfection of PIM1 expressing plasmid into both RD and HeLa cells. It is showed that ectopic expression PIM1 could increase viral titer both in RD and HeLa cells. It was consistent with previously loss of function studies (e.g., as shown in FIGS. 3A and 3B). Furthermore, the inventors determined viral protein VP1 expression level by knockdown or ectopic-expressing PIM1. The results demonstrated that the viral protein VP1 was significantly decreased or increased accordingly after PIM1 depletion and ectopic-expression (e.g., as shown in FIGS. 3C and 3D).

Figure 4F:
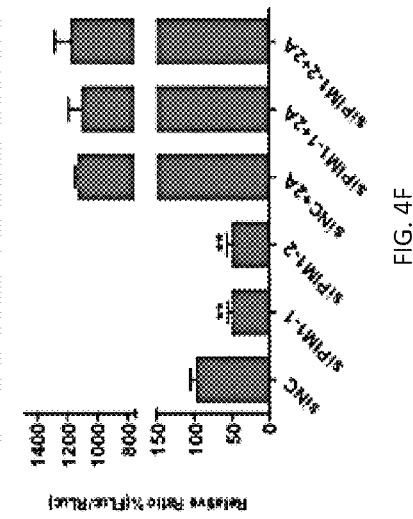
FIG. 4F is a plot showing the relative ratio of Fluc expression to RLuc expression in cells transfected with siPIM1-1 or siPIM1-2, and transfected cells which ectopically express viral protein 2A.
Figure 4E:
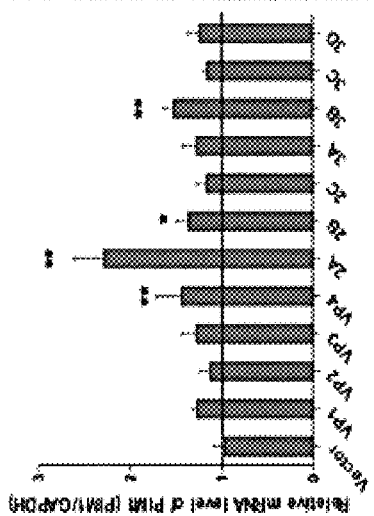
FIG. 4E is a plot showing the relative mRNA level of PIM1 in cells transfected with different viral protein expressing plasmids, and the viral proteins include 2A, 2B, 2C, 3A, 3B, 3C, 3D, VP1, VP2, VP3, and VP4. The results show that viral protein 2A is capable of increasing the mRNA level of PIM1.
Figure 4D:
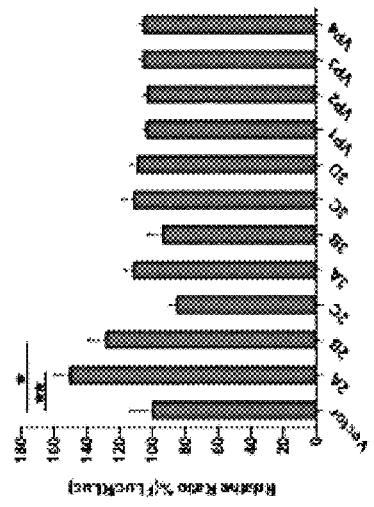
FIG. 4D is a plot showing the relative ratio of FLuc expression to RLuc expression in cells transfected with different viral protein expressing plasmids, and the viral proteins include 2A, 2B, 2C, 3A, 3B, 3C, 3D, VP1, VP2, VP3, and VP4. The results show that viral protein 2A is the most effective protein in increasing the IRES activity.

Enhancing viral IRES activity by PIM1: Enterovirus protein translation is initiated through viral IRES elements in a cap-independent manner. A dicistronic reporter plasmid was used to evaluate EV-A71 IRES activity when PIM1 was modulated (e.g., as shown in FIG. 4A). The relative IRES activity is represented by calculating the ratio of FLuc expression to RLuc expression. As indicated in the materials and methods section, PIM1 was over-expressed or silenced by transfecting with relative plasmid or siRNA and then transfected with pIRES plasmid. EV-A71 IRES activity was analyzed 48 hours after first round transfection. As shown in FIGS. 4B and 4C, over-expression of PIM1 increased the EV-A71 IRES activity to 200% of the control, while knockdown of endogenous PIM1 expression decreases EV-A71 IRES activity to 40% of the control. Also, pIRES was co-transfected and a viral protein expressing plasmid individually. Viral $2A^{pro}$ was the most effective protein that increased the IRES activity (e.g., as shown in FIG. 4D). After all viral protein expression plasmids were transfected into 293T cells, viral $2A^{pro}$ as well as VP4, 2B and 3B stimulated PIM1 expression, while only $2A^{pro}$ significantly increased the mRNA level of PIM1 more than 2 times (e.g., as shown in FIG. 4E). It's highly correlated that PIM1 increased IRES activity through $2A^{pro}$ function. To further address the findings, the inventors then performed the rescue experiments. The inventors silenced PIM1 and then ectopically expressed $2A^{pro}$. $2A^{pro}$ rescued the reduction of IRES activity after knockdown of PIM1 (e.g., as shown in FIG. 4F).

Figure 5A:
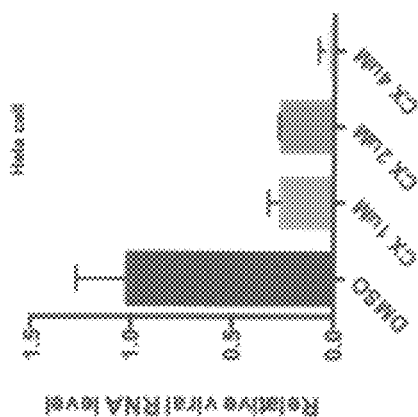
FIG. 5A is a plot showing the relative viral RNA level in RD cells treated with different concentration of the compound CX-6258 (abbreviated as CX in the figure), i.e. 2 µM, 4 µM and 8 µM, according to an embodiment herein.
Figure 5B:
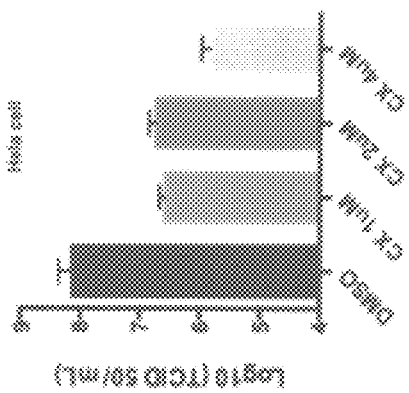
FIG. 5B is a plot showing the relative viral RNA level in HeLa cells treated with different concentration of the compound CX-6258 (abbreviated as CX in the figure), i.e. 1 µM, 2 µM and 4 µM, according to an embodiment herein.
Figure 5C:
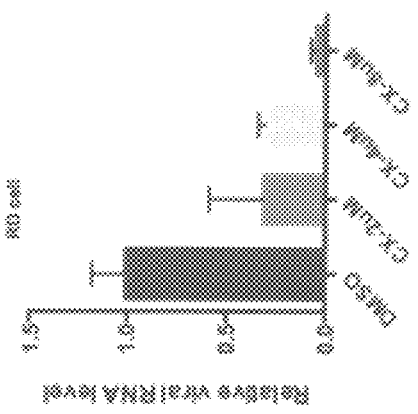
FIG. 5C is a plot showing TCID50 in RD cells treated with different concentration of the compound CX-6258 (abbreviated as CX in the figure), i.e. 2 µM, 4 µM and 8 µM.
Figure 5D:
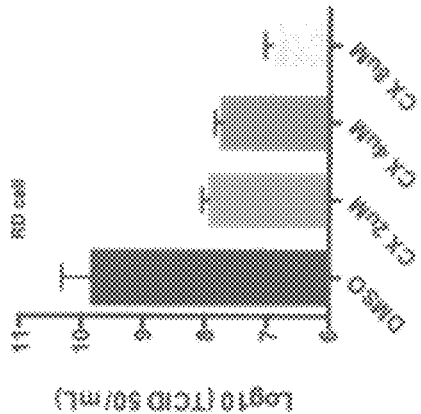
FIG. 5D is a plot showing TCID50 in HeLa cells treated with different concentration of the compound CX-6258 (abbreviated as CX in the figure), i.e. 1 µM, 2 µM and 4 µM.

Suppression of EV-A71 infection by PIM1 inhibitors: To further test whether PIM1 could be the potential drug target against EV-A71 infection, the inventors examined several PIM1 inhibitors (e.g., SGI-1776, CX-6258, AZD-1208) in both RD and HeLa cells. The inhibitors were first tested on cell viability in HEK 293T, RD and HeLa cells by MIT assay. SGI-1776 and CX-6258 inhibited cell growth at a higher concentration, while AZD-1208 did not affect cell growth. RD or HeLa cells were pretreated for 2 hours with indicated inhibitors and concentrations, then infected with EV-A71 for 24 h at MOI 1. As shown in FIGS. 5A to 5F, the VP1 expression level was remarkably repressed by PIM1 inhibitors in a dose-dependent manner. CX-6258 showed the best inhibitory effects in RD cells (e.g., as shown in FIGS. 5A and 5B). CX-6258 was further used as PIM1 inhibitor to determine the extracellular viral mRNA levels as mentioned above. Results showed that after inhibiting PIM1, viral mRNA levels were significantly decreased both in RD and HeLa cells (e.g., as shown in FIGS. 5G and 5H). In addition, the viral titer was also decreased more than $10^3$ after inhibiting PIM1 activity with CX-6258 in RD cell and HeLa cells (e.g., as shown in FIGS. 5I and 5J).

Inhibition of $2A^{pro}$-mediated eIF4G cleavage by CX-6258: To address how PIM1 affects the IRES activity regulated by $2A^{pro}$, the effect of PIM1 on $2A^{pro}$ cleavage activity was considered. IRES-driven translation was activated after the cleavage of eIF4G by $2A^{pro}$ (e.g., as shown in FIG. 6B). PIM1 inhibitor was tested to determine the affect the cleavage of eIF4G after virus infection. As shown in FIG. 6A, RD cells were treated with CX-6258 at different concentrations, and then infected with EV-A71 at MOI 10. After 9 hours p.i., the cleavage of eIF4G was significantly inhibited. To further demonstrate the inside mechanism, HEK 293T cells were firstly treated with CX-6258 for 2 hours, and then co-transfected with a $2A^{pro}$ expressing plasmid for 36 hours. The cleavage of eIF4G was also inhibited with PIM1 inhibitor in a dose-dependent manner (e.g., as shown in FIG. 6C). Similarly, when 293T cells were transfected with the PIM1 expression plasmid for 48 hours, then infected with EV-A71 at MOI 10 for indicated time points. The cleavage of eIF4G was up-regulated in the PIM1 ectopically expressed cells (FIG. 6D).

Figure 7B:
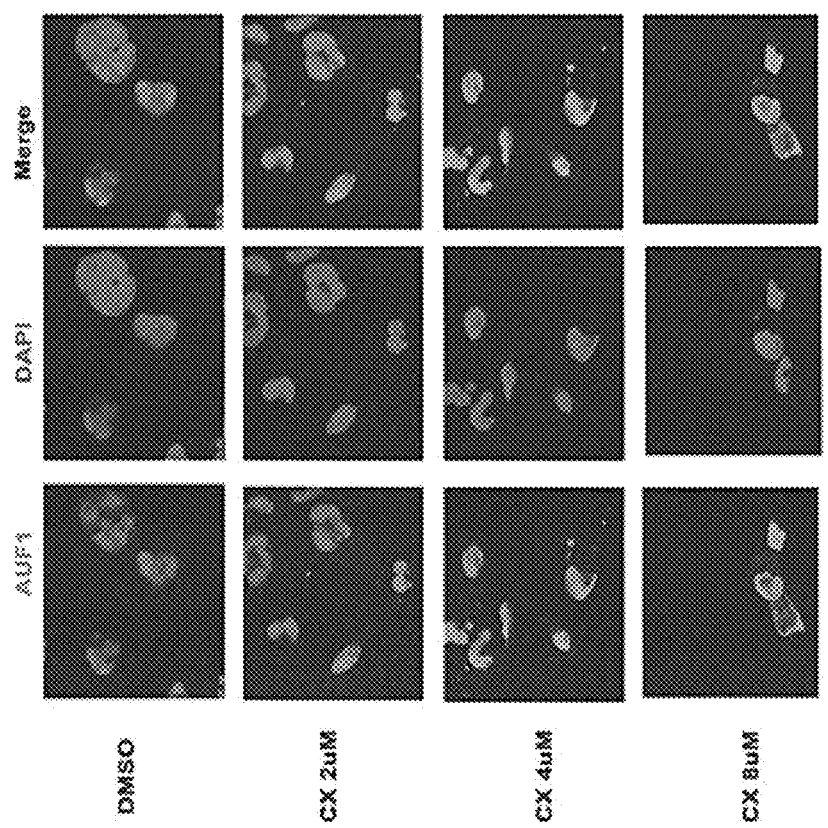
FIG. 7B shows the microscopic images obtained after treated cells with CX-6258 at different concentration, it shows the induced accumulation of AUF1 in cytoplasm by use of a PIM1 inhibitor CX-6258.
Figure 7A:
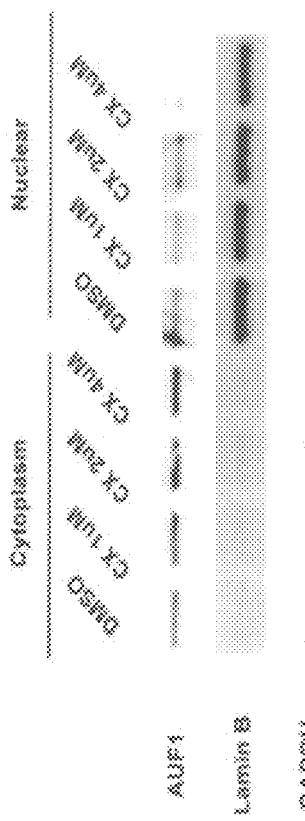
FIG. 7A shows the relative expression of AUF1, Lamin B and GAPDH in cells treated with different concentration of CX-6258.

Induction of the cytoplasmic accumulation of AUF1 by CX-6258: The inventors further explored how PIM1 affected the viral 1IRES activity. After treated cells with PIM1 inhibitor CX-6258 for 2 hours, the inventors isolated the cytoplasm and nuclear proteins and applied fbr western blot assays. The translocation of ITAF factors (e.g., including AUF1, hnRNP K, FBP1, and Sam68) were examined, and it was found that only AUF1, a suppressor of the IRES, was affected by PIM1 inhibitor. The cytoplasm accumulation of AUF1 was significantly increased (e.g., as shown in FIG. 7A). The inventors also used confocal image to examine the cellular distribution of AUF1. Consistently, the inventors revealed that much more AUF1 was accumulated in cytoplasm after the cells were treated with PIM1 inhibitor (e.g., as shown in FIG. 7B).

PIM1 plays a key role in Zika virus infection: To investigate whether PIM1 also exhibits key role in other RNA virus family members, the Zika virus was used as a work model. As shown in FIGS. 8A-C, knockdown of PIM1 by siRNA decreased the expression level of viral envelop protein (e.g., as shown in FIG. 8A, upper panel). On the contrary, ectopic expression of PIM1 promoted viral envelop protein expression (e.g., as shown in FIG. 8A, low panel). Surprisingly, knockdown of PIM1 by siRNA suppressed Zika RNA replication (e.g., as shown in FIG. 8B, left panel) whereas ectopic expression of PIM1 promoted viral RNA replication (FIG. 8B, right panel). Consistently, knockdown or ectopic expression of PIM1 potently suppressed or promoted virus reproduction by measuring the viral genome packaged and secreted in the culture media (e.g., as shown in FIG. 8C), respectively.

Figure 9A:
FIG. 9A shows the relative expression of Zika viral envelop protein (denoted as ZIKV Env) in RD cells or HeLa cells treated with CX-6258 at different concentrations including 1 µM, 2 µM and 4 µM, as compared to vehicle group with DMSO.
Figure 9B:
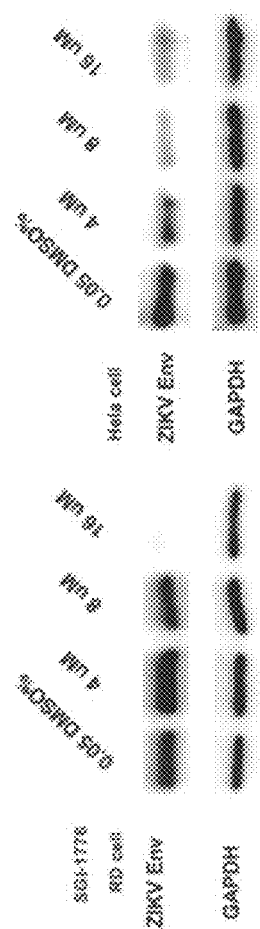
FIG. 9B shows the relative expression of Zika viral envelop protein (denoted as ZIKV Env) in RD cells or HeLa cells treated with SGI-1776 at different concentrations including 4 µM, 8 µM and 16 µM, as compared to vehicle group with DMSO.
Figure 9C:
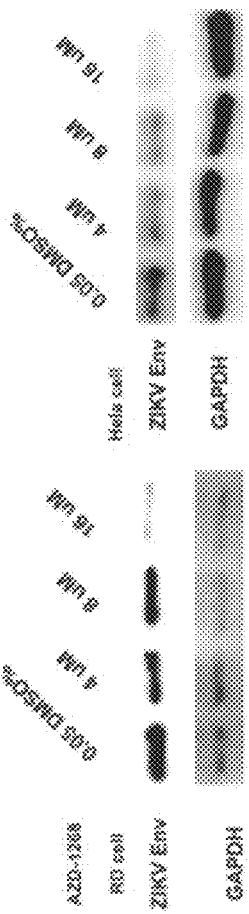
FIG. 9C shows the relative expression of Zika viral envelop protein (denoted as ZIKV Env) in RD cells or HeLa cells treated with AZD-1268 at different concentrations including 4 µM, 8 µM and 16 µM, as compared to the vehicle group with DMSO.

Inhibition of Zika virus infection by PIM1 inhibitors: To further address if PIM1 inhibitors display potent antiviral effects on Zika virus, the inventors treated RD cells with different PIM1 inhibitors including CX-6528, SGI-1776 and AZD-1268, and inhibited the cells with Zika virus, as shown in FIGS. 9A to 9C, all the inhibitors markedly suppressed the expression of viral envelop protein, suggesting PIM1 inhibitors are also protnising antiviral agents against flavivirus infections.

Discussion

In various embodiments, the global gene profiles between EV-A71 infected and mocked infected RD cells were revisited. 425 differentially regulated genes (>1.5 fold changes) were identified in response EV-A71 infection in which 267 genes were upregulated and 158 genes were downregulated.

As described herein PIM1 is a positive regulator for EV-A71 replication. PIM1 elevated EV-A71 replication through up-regulated the IRES activity by increasing $2A^{pro}$-mediated eIF4G cleavage and blocking AUF1 translocation from nucleus to cytosol. More importantly, PIM1 inhibitors potently repressed EV-A71 infection. Particularly, CX-6258 reduced the viral titer over 1,000 times that has not been reported by any tested agents.

Previously, different expression patterns were observed, and many novel host genes regulated by EV-A71 infection were identified, including those involved in immune response, ER stress, and vesicular trafficking. It had been observed that the up-regulation of apoptotic genes response to EV-A71 infection by analyzing 10,692 genes profiles in infected human SF268 cells. Also, there is a trend to inhibit cell apoptosis and cell growth arrest by analyzing 7600 genes in EV-A71 (strain MS/7423/87, B2 sub-genotype) infected RD cells. RNAi screening had been used to identify 256 host factors involved in EV-A71 replication in RD cells.

In order to identify host genes important for EV-A71 infection, one or more embodiments described herein analyzed the transcription profile of 28,869 genes in EV-A71 infected and mock infected RD cells at 6 hours p.i.. The change of apoptosis related gene profiles were not be observed. EV-A71 viral RNA replicate at high rate and viral protein start to be extensively expressed at this time point; whereas the CPE was not observed at this time points. This may explain why apoptosis related genes were not altered.

It was particular interesting to find out the PIM1, a kinase involved in many important biological processes and never been reported in the process of EV-A71 infection, was up-regulated following EV-A71 infection. PIM1 is a serine/threonine kinase which is involved in cell survival pathways and implicated in a wide variety of human diseases including cancer, inflammatory disorders, and ischemic diseases. Moreover, PIM1 was also found to be linked with viral transcription activation and modulate virus latency and productive infection. For the first time, the various embodiments described herein can establish relationships between PIM1 kinases and EV-A71 infection. Modulation of PIM1 level by specific siRNAs or expression plasmid demonstrated that PIM1 expression increased the level of viral replication (e.g., as shown in FIGS. 2 and 3).

The IRES-driven translation plays a key role in synthesis of viral proteins during EV-A71 infection. Further, PIM1 promotes the IRES activity upon EV-A71 infection by using both gain- and loss-of-function studies (e.g., as shown in FIGS. 4A-F). EV-A71 infection increased PIM1 expression level (e.g., as shown in FIG. 4E), and the increased PIM1 expression promoted EV-A71 replication (e.g., as shown in FIGS. 3A-D). Additionally, three PIM1 inhibitors (e.g., SGI-1776, CX-6258, AZD-1208) showed a high potency to inhibit viral infectivity of EV-A71 (e.g., as shown in FIGS. 5G-J). Both viral RNA levels and viral titer were dramatically decreased in a dose-dependent manner with a good perspective clinical therapeutic usage (e.g., as shown in FIGS. 5G-J).

EV-A71 recruits many host factors to facilitate viral protein synthesis via IRES-driven translation. HscVO binds the full length of viral RNA and promotes the IRES activity.

As described herein, $2A^{pro}$ can rescue the silenced PIM1 reduced IRES activity. $2A^{pro}$ is one of the well-known protease to cleavage eIF4G for promoting viral replication. The cleaved eIF4G was separated into two parts, and one of them directly binds to IRES and assists the translation process. Additionally, PIM1 inhibitor CX-6258 inhibited the cleavage of eIF4G upon EV-A71 infection (e.g., as shown in FIGS. 6A-D). Furthermore, PIM1 inhibitor inhibited the eIF4G cleavage by $2A^{pro}$ in a dose-dependent manner (e.g., as shown in FIGS. 6A-D). In addition, PIM1 plays a crucial role in control of AUF1 cytosol translocation (e.g., as shown in FIGS. 7A-B).

Thereby PIM1 contributes to EV-A71 infection trough two distinct mechanisms. PIM1 exhibits a positive role in EV-A71 infection through enhancing the IRES activity by stimulating $2A^{pro}$-mediated eIF4G cleavage and blocking AUF1 cytosol translocation. Also, PIM1 inhibitor CX-6258 decreased viral reproduction over 1,000 times, providing a potent antiviral agent for potential clinic settings in the future.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

It is, of course, not possible to describe every conceivable combination of components, products and/or methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method of reducing replication of an EV-A71 or Zika virus, the method comprising: administering, to a biological cell afflicted with the EV-A71 or Zika virus, an effective antiviral amount of a PIM1 inhibitor, wherein the PIM1 inhibitor is a ribonucleic acid interfering ribonucleic acid, or a compound comprising a structure of Formula (I), Formula (II), Formula (III) or a salt or solvate thereof:

Formula (I)

Formula (II)

Formula (III)

2. The method of claim 1, wherein the effective antiviral amount of PIM1 inhibitor suppresses an internal ribosome entry site activity of the viral infection by decreasing protein 2A proteinase-mediated cleavage of eukaryotic initiation factor G (eIF4G).

3. The method of claim 1, wherein the effective antiviral amount of PIM1 inhibitor blocks ARE/poly(U)-binding/degradation factor 1 (AUF1) translocation from a nucleus of the biological cell to a cytosol of the biological cell.

4. A method of reducing an internal ribosome entry site activity in a biological cell afflicted with an EV-A71 or Zika virus, the method comprising: decreasing a level of PIM1 within the biological cell by a PIM1 inhibitor, wherein the PIM1 inhibitor is a ribonucleic acid, or a compound comprising a structure of Formula (I), Formula (II), Formula (III) or a salt or solvate thereof:

Formula (I)

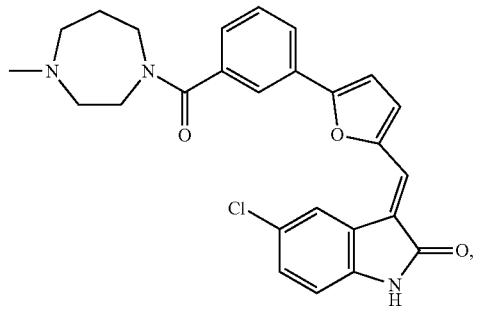

Formula (II)

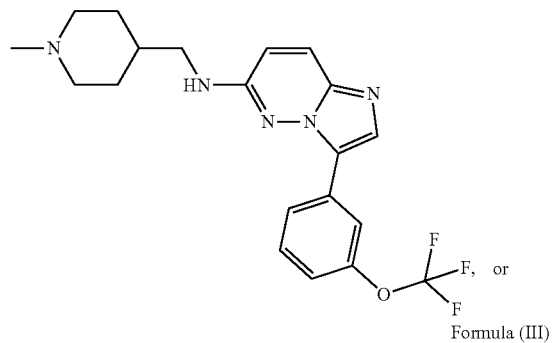

or

Formula (III)

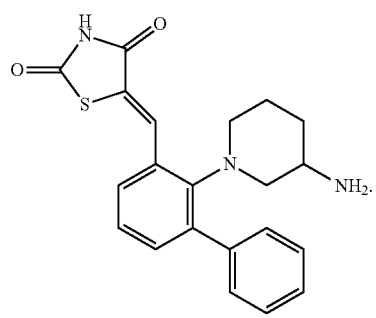

5. The method of claim 4, wherein the effective antiviral amount of PIM1 inhibitor suppresses the internal ribosome entry site activity by decreasing protein 2A proteinase mediated cleavage of eukaryotic initiation factor 4 G (eIF4G).

* * * * *